United States Patent [19]

Anderson et al.

[11] Patent Number: 4,622,638

[45] Date of Patent: Nov. 11, 1986

[54] IONIZATION PROBE OUTPUT INTERFACE CIRCUIT

[75] Inventors: Robert L. Anderson, Saline; William R. McDonald, Westland, both of Mich.

[73] Assignee: Ford Motor Company, Dearborn, Mich.

[21] Appl. No.: 564,442

[22] Filed: Dec. 22, 1983

[51] Int. Cl.[4] .............................................. F02P 5/14
[52] U.S. Cl. ................................. 364/431.08; 123/425; 123/415; 324/464
[58] Field of Search .................... 364/550, 556, 431.03, 364/431.08; 73/35, 115; 123/415, 416, 425, 435, 494; 324/459, 460, 464

[56] References Cited

U.S. PATENT DOCUMENTS

| 4,288,749 | 9/1981 | Murtin ................................ 324/464 |
| 4,304,203 | 8/1981 | Garcea et al. . |
| 4,340,021 | 7/1982 | Oshiage et al. .................... 123/415 |
| 4,345,154 | 8/1982 | Bainbridge . |
| 4,377,140 | 3/1983 | Latsch . |
| 4,488,528 | 12/1984 | Morikawa ........................ 123/425 |

FOREIGN PATENT DOCUMENTS

| 1512213 | 5/1978 | United Kingdom . |
| 2060062A | 4/1981 | United Kingdom . |

Primary Examiner—Parshotam S. Lall
Attorney, Agent, or Firm—Peter Abolins; Robert D. Sanborn

[57] ABSTRACT

The capacitive effect of a coaxial cable coupled to an ionization probe is reduced by an operational amplifier which applies a constant bias voltage to the coaxial cable.

3 Claims, 7 Drawing Figures

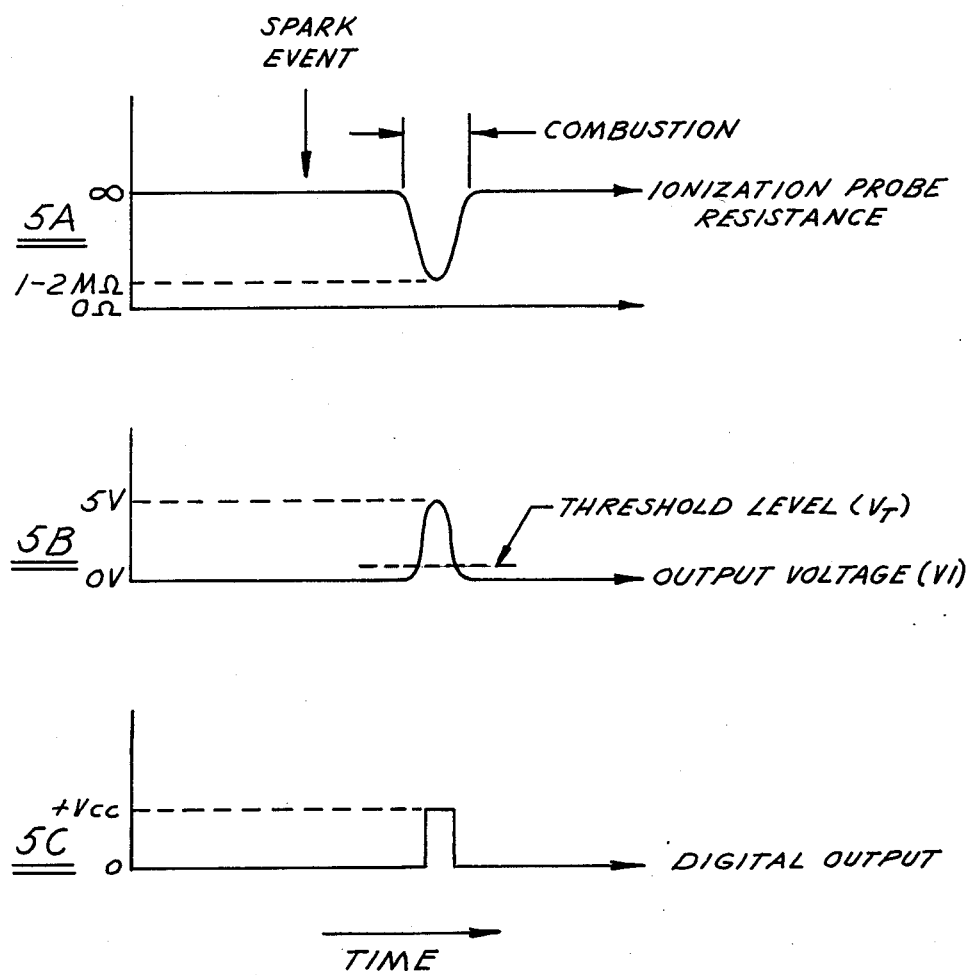

IONIZATION PROBE OUTPUT INTERFACE CIRCUIT

BACKGROUND OF THE INVENTION

1. Field of the Invention

This invention relates to controlling an engine using an ionization probe to detect cylinder combustion.

2. Prior Art

It is known to control various engine operating parameters, such as composition of exhaust emissions, in accordance with the relative time of occurrence of the combustion chamber peak pressure and piston top dead center during the combustion process. One of the known methods of detecting combustion chamber pressure is using an ionization probe placed in the combustion chamber.

For example, U.S. Pat. No. 4,304,203 issued to Garcea et al; U.S. Pat. No. 4,377,140 issued to Latsch and British Pat. Nos. 1,512,213 and 2,060,062A teach the use of an ionization sensing probe to control the combustion cycle in an internal combustion engine. Closed loop control using an ionic current sensor to determine the end of the ignition phase of a combustible mixture in an internal combustion engine can be used to adapt ignition timing to compensate for conditions such as thermal status of the engine, characteristics of the fuel and of the combustion air, engine wear and so on.

U.S. Pat. No. 4,345,154 issued to Bainbridge teaches an ionization sensing device to detect harmful gases in a gaseous medium. To compensate for erratic changes in the electrical output signals of the sensing cell caused by variations in the flow of gas, a bias voltage is impressed upon the sensing device.

To improve use of an ionization probe in connection with an engine control system, it is desirable to eliminate the cable capacitance effects of the cable coupling the ionization probe to the electronic engine control. The ionization probe usually includes a metallic probe that is inserted through the cylinder wall and is electrically insulated from the metal cylinder block. When combustion occurs in the cylinder, a number of free ions are created in the flame front. The free ions in the flame front cause a current to flow and result in a decrease in the effective resistance between the probe and the cylinder walls. Typical resistance changes are from open circuit, indicating no combustion, to one to two megohms during combustion. The probe is used to measure time of arrival of the flame front relative to the spark event. The time of arrival data is used to determine the quality of the burn cycle.

The probe has high impedance and the signal wire to the probe must be shielded to prevent noise pickup. This is particularly true in automotive applications where the engine control module must be remotely located from the sensor probe and there is the possibility of noise pickup from the ignition system.

It is known to use a relatively high impedance sensing resistor, for example one megohm, in series with the sensing probe (see FIG. 1). The drawback to this approach is the relatively slow time response that occurs as a result of the high impedance and the capacitance of the shielded coaxial cable lead.

For example, if the series resistance is one megohm and the capacitance of the coaxial cable is about 500 pico-farads, the time constant, due to the capacitance of the cable is about 500 microseconds. At 6000 rpm of engine operation, 500 microseconds is equivalent to 18° of crank rotation. Advantageously, good engine control requires that the time of arrival of the flame front be measured to within at least plus or minus one degree of crank rotation. Accordingly, a technique which measures flame front arrival to within 18° of crank rotation is not acceptable.

It would be desirable to keep the time response of the sensor and interface circuit to a much smaller amount and to reduce the capacitive effect of the cable.

SUMMARY OF THE INVENTION

An ionization probe interface circuit improves the response time of an ionization probe by eliminating the capacitive effect of a coaxial cable coupling the ionization probe and the ionization probe interface circuit. The ionization probe interface circuit includes an operational amplifier for applying a constant bias voltage on the coaxial cable. The voltage bias placed between the ionization probe and the engine block keeps the probe voltage substantially constant thereby substantially reducing the capacitive effect of the cable and improving the speed of response of the ionization probe.

The operational amplifier provides that the voltage at the ionization probe is constant and that current changes are a result of resistance changes at the ionization probe. Accordingly, if there is no voltage change, then the size of the capacitance, even if large, has no affect on system response. The current change at the ionization probe is sensed by the operational amplifier which amplifies current. In contrast to applying a constant voltage bias at the ionization probe as taught by this invention, the prior art allowed a voltage change across the ionization probe.

BRIEF DESCRIPTION OF THE DRAWINGS

FIGS. 5A–5C are a graphical representation of spark event voltage, output voltage of the current detector, and output voltage of the level detector, with respect to time, in accordance with an embodiment of this invention.

DETAILED DESCRIPTION OF THE INVENTION

Figure 1:
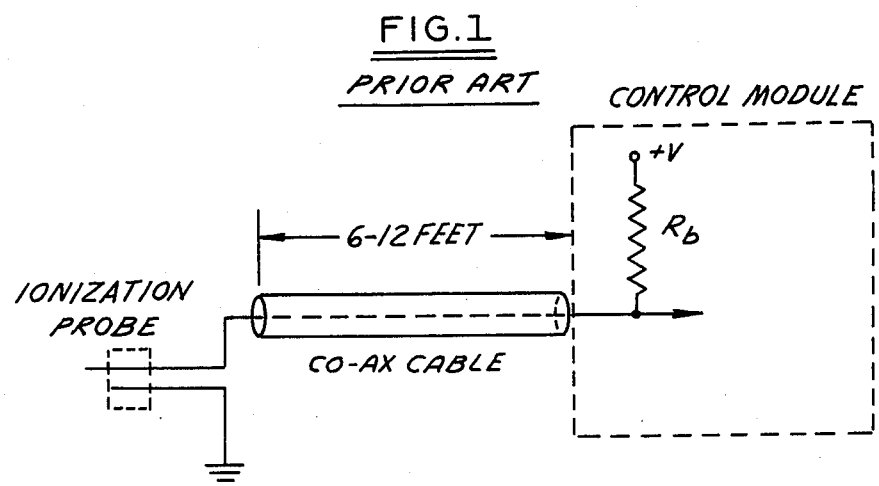
FIG. 1 is a block diagram of a prior art embodiment for sensing the output of an ionization probe.
Figure 2:
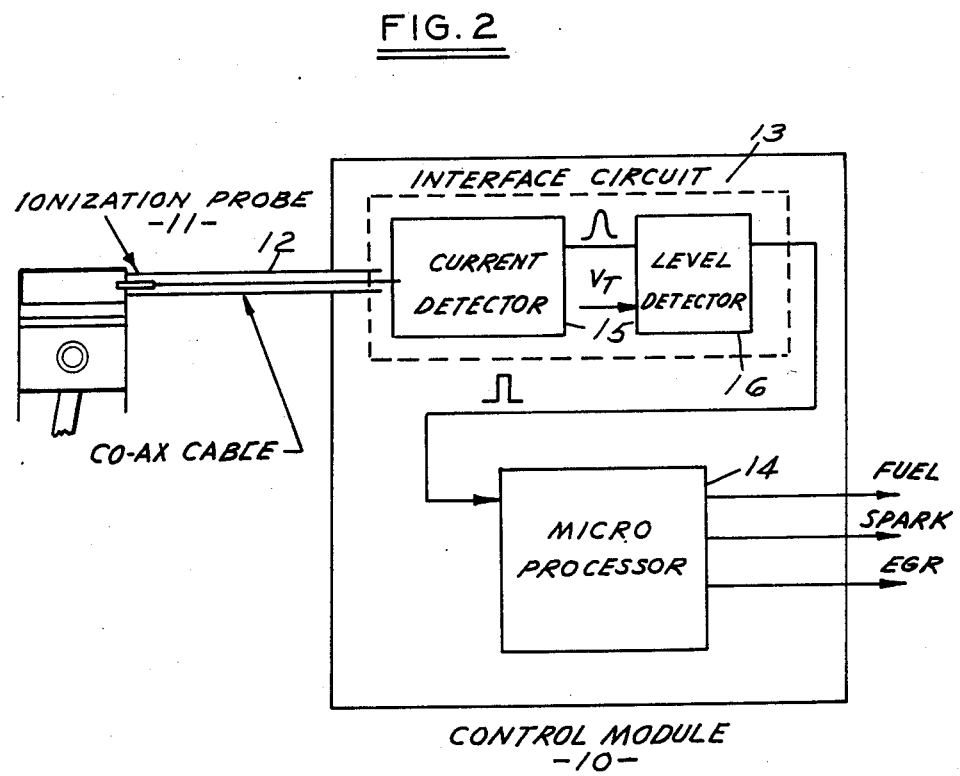
FIG. 2 is a block diagram of an interface circuit of an engine control module in accordance with an embodiment of this invention.

Referring to FIG. 2, a control module 10 is coupled to an ionization probe 11 through a coaxial cable 12. Control module 10 includes an interface circuit 13 coupled to a microprocessor 14. Interface circuit 13 includes a current detector 15 coupled to coaxial cable 12 and a level detector 16 coupled to current detector 15. Interface circuit 13 applies a constant bias voltage to cable 12 and produces an output voltage pulse that is in response to the ionization current that flows from ionization probe 11 through coaxial cable 12 to current detector 15. This pulse triggers level detector 16 to produce a square wave pulse that provides a rising and falling edge signal coincident with the start and end of combustion in the cylinder coupled to ionization probe 11. This signal is then fed to a microprocessor controller 14 which has software strategy to adjust spark timing, EGR and the fuel/air mixture to produce advantageous engine operation.

Figure 3:
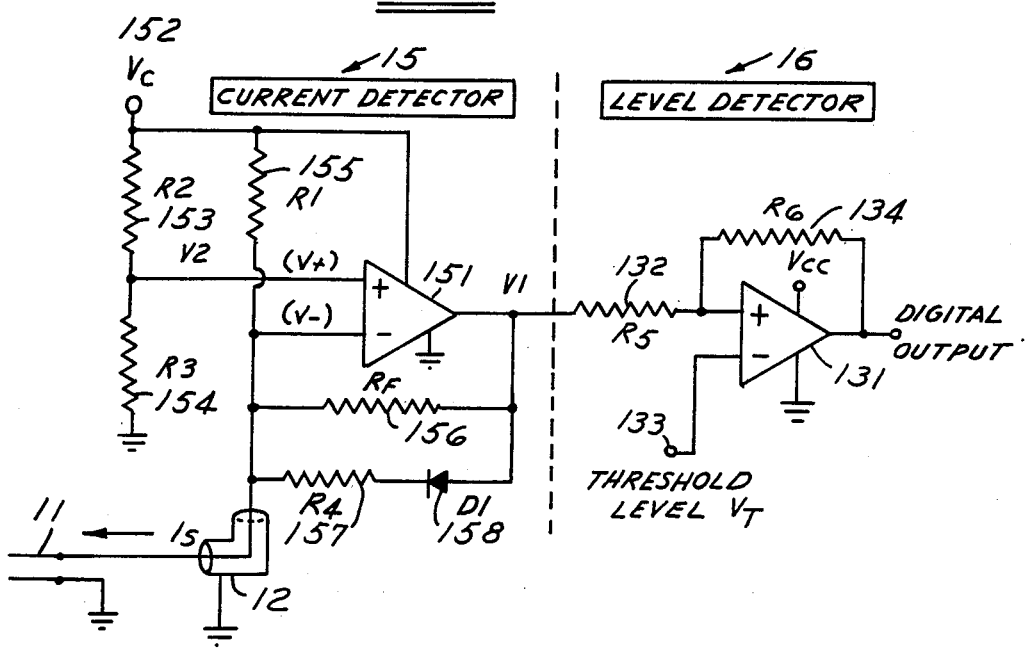
FIG. 3 is a schematic diagram of the current detector and level detector blocks of FIG. 2 in accordance with an embodiment of this invention.

Referring to FIG. 3, current detector 15 includes an operational amplifier 151 having a positive input coupled to a voltage source 152 through a resistor 153 and coupled to ground through a resistor 154. The negative input to amplifier 151 is coupled to voltage source 152 through a resistor 155. A feedback resistor 156 is coupled between the output of amplifier 151 and the negative input of amplifier 151. In parallel with feedback resistor 156 is the series combination of a resistor 157 and a diode 158. The negative input of operational amplifier 151 is coupled to coaxial cable 12.

Level detector 16 includes an operational amplifier 131 having a positive input coupled to the output of operational amplifier 151 through a resistor 132. The negative input of operational amplifier 131 is coupled to a threshold level voltage 133. A feedback resistor 134 is coupled between the output of amplifier 131 and the positive input of amplifier 131.

In operation, current detector 15 uses operational amplifier 151 to convert the change in probe resistance into an output voltage V1. The values of resistor 156 and resistor 155 are selected to equal the probe resistance during combustion. Resistors 153 and 154 are selected so that the output of operational amplifier 151 is slightly positive to assure the amplifier is in the linear region of operation. As ionization probe 11 resistance is lowered, increasing the sensor current flowing in coaxial cable 12, the output voltage V1 of operational amplifier 151 will increase to keep the negative input to operational amplifier 151 within a few microvolts of the positive voltage input to operational amplifier 151. Thus, the negative input voltage of operational amplifier 151 with respect to ground, hence the sensor bias voltage, varies very little even though the probe current has increased. The actual sensitivity of the output voltage V1 of operational amplifier 151 to a change in the sensor resistance, $R_S$, of ionization probe 11, depends upon the ratio of the sensor resistance of ionization probe 11 to the magnitude of feedback resistor 156. If the sensor resistance equals feedback resistor 156 and if resistor 155 equals feedback resistor 156, output voltage V1 will be approximately equal to source voltage 152 divided by 2. If the sensor resistance is greater than the feedback resistance 156, then output voltage V1 will decrease toward zero as the sensor resistance increases (see FIG. 4). If the sensor resistance is less than feedback resistor 156, output voltage V1 will increase to more than twice the source voltage 152 until the operational amplifier 151 saturates.

Figure 4:
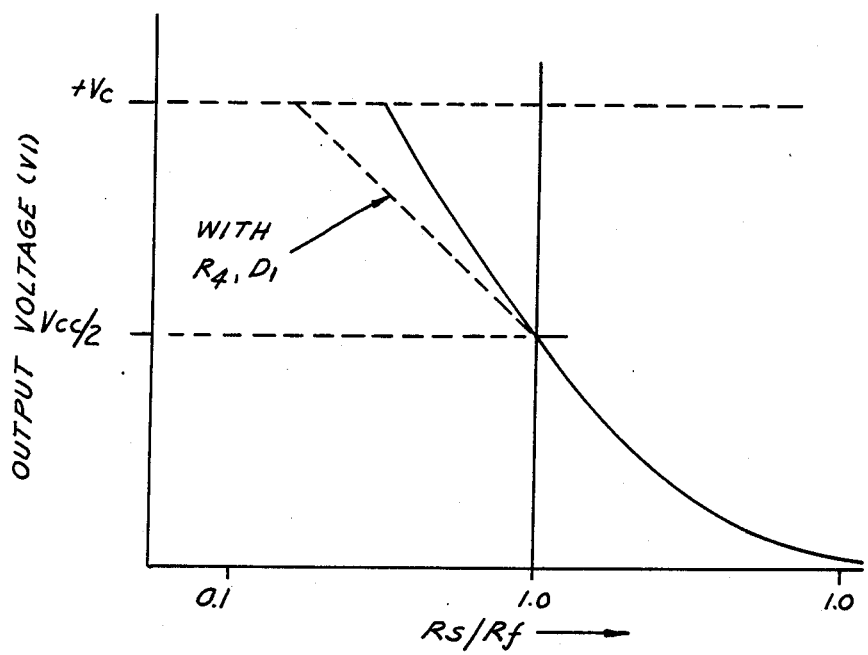
FIG. 4 is a graphical representation of current detector output voltage versus a feedback resistance ratio.

Resistor 157 and diode 158 are advantageously used to extend the dynamic range of the current as shown in FIG. 4. When the output voltage V1 of operational amplifier 151 is larger than approximately one-half of VCC, resistor 157 becomes another feedback resistor in parallel with resistor 156. Typically, resistor 157 is equal to about one-fourth of the magnitude of feedback resistor 156. This effectively reduces the circuit gain for values of the sensor resistor less than the values of feedback resistor 156 and effectively increases the dynamic range of operation.

The comparative value ($V_T$) of threshold voltage 133 is set just above the open circuit value of V1 so that any decrease in sensor resistance, corresponding to an increase in output voltage V1, will produce a comparator output signal as shown in FIG. 5. Line 5A of FIG. 5 shows a decrease in sensor resistance of the ionization probe from infinity to about 1 to 2 megohms after the spark event and during combustion. Line 5B of FIG. 5 shows a corresponding increase in output voltage V1 from zero to about 5 volts during the reduction of ionization probe resistance. With a threshold level, $V_T$, set below 5 volts, the output of level detector 16 is shown as a square wave in line 5C extending between zero and voltage $V_{CC}$.

The speed of response of the circuit is limited only by the bandwidth of the operational amplifiers used in current detector 15 and level detector 16. Typically, this can be about 500 kHz to about 1 mHz. This corresponds to a response time of 1 to 2 microseconds, which translates to 0.037–0.074 degrees of crank rotation at 6000 rpm. This is acceptable for engine control usage and is about a 500 to 1 improvement over other known alternatives.

Various modifications and variations will no doubt occur to those skilled in the arts to which this invention pertains. For example, the particular configuration of the level detector may be varied from that disclosed herein. These and all other variations which basically rely on the teachings through which this disclosure has advanced the art are properly considered within the scope of this invention.

We claim:

1. An ionization probe interface circuit means for improving the response time of an ionization probe by eliminating the capacitive effect of a coaxial cable coupling said ionization probe and said ionization probe interface circuit means, said ionization probe interface circuit means including:
   an operational amplifier means for applying a constant bias voltage to said coaxial cable, said operational amplifier means applying a positive voltage bias to said ionization probe with respect to a ground potential;
   current detector means coupled to said ionization probe through said coaxial cable for producing a voltage pulse in response to a current output from said ionization probe;
   a level detector coupled to said current detector means for producing a square wave pulse in response to a voltage output from said current detector means; and
   a microprocessor means coupled to said level detector for generating signals controlling engine operating parameters in response to the square wave output of said level detector.

2. An ionization probe interface circuit means as recited in claim 1 wherein:
   said current detector includes:
   a first operational amplifier, for performing as a comparator, having a negative input coupled to said coaxial cable and coupled to a supply voltage through a first resistor, and having a positive input coupled to a supply voltage through a second resistor and coupled to ground through a third resistor,
   a feedback resistor coupled between the output and said positive input of said operational amplifier; and
   a series combination of a fourth resistor and a diode coupled in parallel with said feedback resistor.

3. An ionization probe interface circuit means as recited in claim 2 wherein said level detector includes:
   a second operational amplifier, for performing as a comparator, having a positive input coupled through a fifth resistor to the output of said first operational amplifier, a negative input coupled to a voltage threshold level and an output coupled to said positive input of said second operational amplifier through a sixth resistor.

* * * * *